(12) United States Patent
Xue

(10) Patent No.: US 9,788,796 B2
(45) Date of Patent: Oct. 17, 2017

(54) SYSTEM AND METHOD OF ADAPTIVE INTERPRETATION OF ECG WAVEFORMS

(71) Applicant: General Electric Company, Schenectady, NY (US)

(72) Inventor: Joel Qiuzhen Xue, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 14/885,020

(22) Filed: Oct. 16, 2015

(65) Prior Publication Data

US 2017/0105683 A1    Apr. 20, 2017

(51) Int. Cl.
 *A61B 5/04* (2006.01)
 *A61B 5/00* (2006.01)
 *A61B 5/0402* (2006.01)
 *A61B 5/044* (2006.01)

(52) U.S. Cl.
 CPC .......... *A61B 5/7267* (2013.01); *A61B 5/0402* (2013.01); *A61B 5/044* (2013.01); *A61B 5/04012* (2013.01); *A61B 5/7475* (2013.01)

(58) Field of Classification Search
 USPC .................................... 600/509, 523; 702/19
 See application file for complete search history.

(56) References Cited

U.S. PATENT DOCUMENTS

| 2006/0079795 | A1* | 4/2006 | Busche | A61B 5/0452 600/509 |
| 2007/0027630 | A1* | 2/2007 | Sanchez | G06F 19/28 702/19 |
| 2013/0085405 | A1* | 4/2013 | Bera | A61B 5/044 600/515 |

* cited by examiner

*Primary Examiner* — Nicole F Johnson
(74) *Attorney, Agent, or Firm* — Andrus Intellectual Property Law, LLP

(57) ABSTRACT

A cluster database includes existing ECG datasets organized into clusters, wherein each existing ECG dataset includes an existing ECG waveform with at least one corresponding existing feature and existing interpretation. Each cluster is comprised of existing ECG datasets having a common existing feature. The cluster training module is executable by the processor to receive a new ECG waveform and a feature extracted from the new ECG waveform. The cluster training module then selects a cluster interpretation module based on the feature, wherein the cluster interpretation module is trained on one of the clusters from the cluster database. The cluster training module processes the new ECG waveform and/or the feature to provide a cluster interpretation output. The cluster interpretation output is then displayed on the user interface, and the cluster training module receives clinician input via the user interface accepting or rejecting the cluster interpretation output.

19 Claims, 5 Drawing Sheets

SYSTEM AND METHOD OF ADAPTIVE INTERPRETATION OF ECG WAVEFORMS

BACKGROUND

Systems and methods for interpreting ECG waveforms are currently available to assist a clinician in interpreting waveforms and assessing patient cardiac health based on ECG waveforms. Currently available systems and methods generally process ECG waveform data and provide suggested interpretations based thereon. These currently available systems and methods are generally trained offline using databases of existing ECG waveform data. Thus, updating and/or expanding existing interpretation methods and systems generally requires offline training and development, and then the launch of a new product version or a product update.

SUMMARY

The present invention alleviates problems recognized by the inventor with systems and methods currently available for interpretation of ECG waveforms. For example, the present inventor has recognized that systems and methods for interpretation of ECG waveforms could be improved by utilizing recently acquired waveform interpretations to train and update the interpretation systems and methods. Moreover, the present inventor has recognized that the periodic issuance of new system versions and/or updates is cumbersome and not ideal. For example, the installation of new versions or updates requires additional effort on the part of the supplier and the user in order to install the new version and/or update. Moreover, in between the timing of new versions and/or updates, the system is not being optimized because new information is generated that could be, but is not, used as feedback to improve the system and/or method. With the recognition of these problems in mind, the inventor has developed the system and method disclosed herein. This summary is provided to introduce a selection of concepts that are further described below in the Detailed Description. This summary is not intended to identify key or central features of the claimed subject matter, nor is it intended to be used as an aid in limiting the scope of the claimed subject matter.

In one embodiment, a system for adaptive interpretation of ECG waveforms includes a processor, a cluster database, a user interface, and a cluster training module. The cluster database includes existing ECG datasets organized into clusters, wherein each existing ECG dataset includes an existing ECG waveform with at least one corresponding existing feature and existing interpretation. Each cluster is comprised of existing ECG datasets having a common existing feature. The cluster training module is executable by the processor to receive a new ECG waveform and a feature extracted from the new ECG waveform. The cluster training module then selects a cluster interpretation module based on the feature, wherein the cluster interpretation module is trained on one of the clusters from the cluster database. The cluster training module processes the new ECG waveform and/or the feature to provide a cluster interpretation output. The cluster interpretation output is then displayed on the user interface, and the cluster training module receives clinician input via the user interface accepting, or rejecting the cluster interpretation output.

In one embodiment for adaptive interpretation of ECG waveforms, a new ECG waveform is received and at least one feature is extracted from the new ECG waveform. A cluster interpretation module is then selected based on the feature, and the new ECG waveform and/or the extracted feature are processed to provide a cluster interpretation output. The method further includes displaying the cluster interpretation output on a user interface, receiving a clinician input accepting or rejecting the cluster interpretation output, and further training the cluster interpretation module based on the clinician input.

A non-transitory computer readable medium having computer-executable instructions stored thereon is presented herein, wherein in one embodiment, the instructions include the step of receiving a new ECG waveform, extracting at least one feature from the new ECG waveform, selecting a cluster interpretation module based on the feature, and processing, the new ECG waveform and/or the extracted feature with the cluster interpretation module to provide a cluster interpretation output. The cluster interpretation module is trained on a cluster from a cluster database of existing ECG datasets, wherein each existing ECG dataset includes an existing ECG waveform with at least one corresponding existing feature and existing interpretation, and wherein each cluster is comprised of ECG datasets having a common existing feature. The instructions may further include displaying the cluster interpretation output on a user interface, receiving a clinician input accepting or rejecting the cluster interpretation output, and further training the cluster interpretation module based on the clinician input.

Various other features, objects and advantages of the invention will be made apparent from the following description taken together with the drawings.

BRIEF DESCRIPTION OF THE DRAWINGS

The drawings illustrate the best mode presently contemplated of carrying out the disclosure. In the drawings.

DETAILED DESCRIPTION

Figure 1:
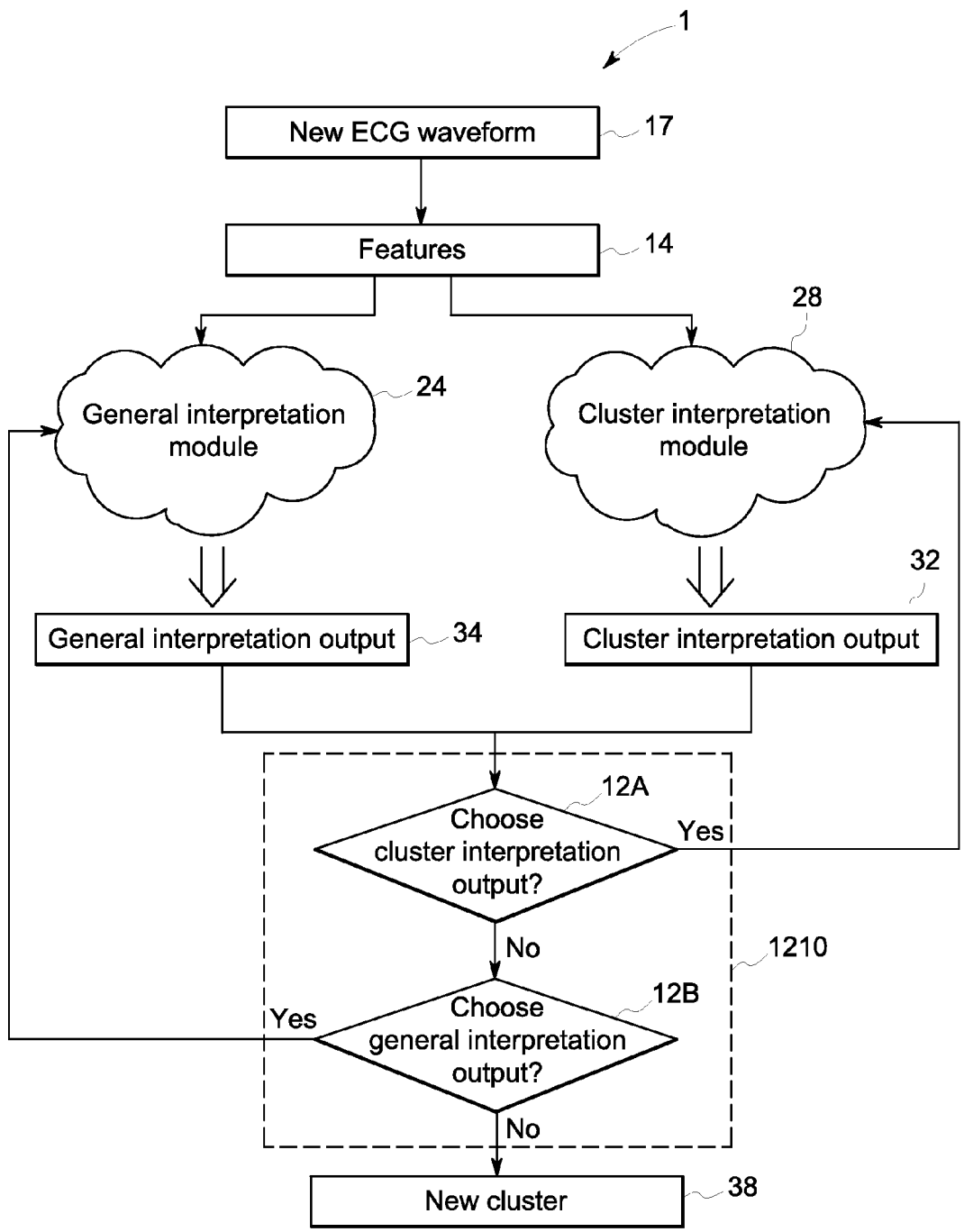
FIG. 1 depicts a flowchart of an exemplary method of adaptive interpretation of ECG waveforms.
Figure 2:
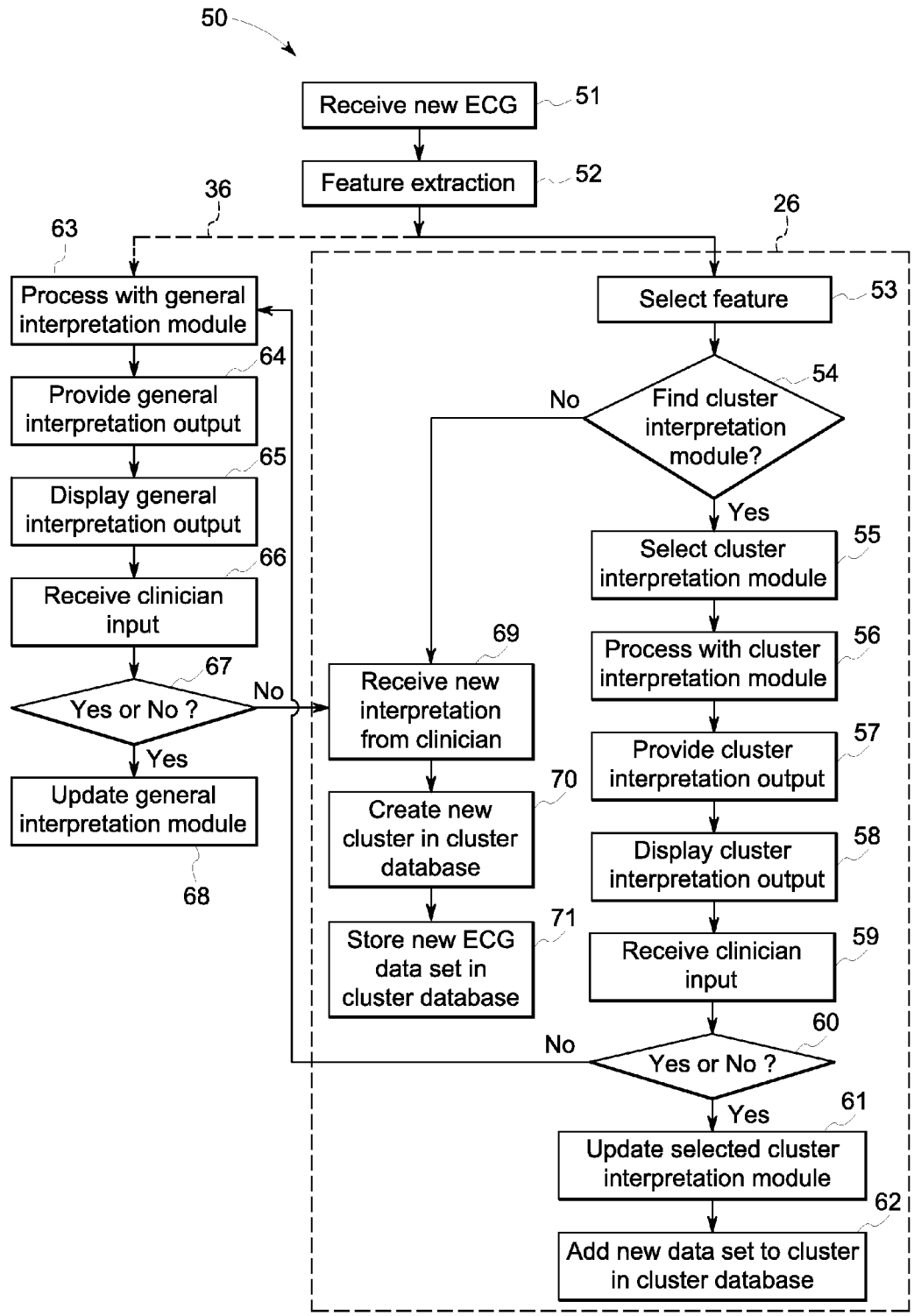
FIG. 2 depicts a flowchart of another embodiment of a method of adaptive interpretation of ECG waveforms.

FIG. 1 diagrammatically exemplifies a system 1 for adaptive interpretation of ECG waveforms. FIG. 2 is a flowchart depicting a corresponding method 50 adaptive interpretation of ECG waveforms. In FIG. 1, a new ECG waveform 17 is received. The new ECG may be, for example, an ECG recording from an ECG monitoring device. The new ECG waveform 17 may be comprised of data resulting from any of various types of ECG tests, and may be in any of multiple data forms available. For example, the new ECG waveform 17 may be a 12-lead ECG, such as a ten second 12-lead resting ECG, which is a commonly performed diagnostic ECG test. Alternatively, the new ECG 17 may be produced by an alternative lead arrangement, such as an abbreviated lead arrangement or a Holter lead arrangement. In still other embodiments, the new ECG waveform 17 may be a derived set of ECG waveforms, such as a derived 12-lead ECG calculated from ECG data collected using a reduced set of ECG leads. Such systems and methods of deriving 12-lead ECGs from alternate electrode configurations are known in the art, and include, for example, the 12RL system by General Electric Company of Schenectady, N.Y., or EASI system produced by Koninklijke Philips N. V. of Amsterdam, Netherlands.

One or more features 14 are extracted from the new ECG waveform 17, such as by any of numerous feature extraction methods and systems known in the art for extracting features from ECG waveforms. As will be understood by a person of ordinary skill in light of this disclosure, and as exemplified, with respect to the existing features 5 of the existing waveforms 4, the features 14 may describe any aspect or element of the ECG morphology or sinus rhythm, and may focus on elements or aspects of the ECG waveforms that deviate from a normal ECG waveform. The features 14 may also be any set, or group, of morphological and/or rhythm characteristics that have clinical significance when appearing simultaneously—e.g., QRS, ST, and T wave morphologies and/or rhythm patterns that, together, indicate a cardiac condition of the patient.

The new ECG waveform data 17 and corresponding feature(s) 14 then interpreted by two different interpretation modules, the general interpretation module 24 and the cluster interpretation module 28. As discussed in detail herein, the interpretation modules 24, 28 are trained modules generated by any number of available machine learning techniques, such as neural networks, decision trees, or statistical classification algorithms. As will be understood by a person of ordinary skill in the art reviewing this disclosure, a neural network (or artificial neural network) refers to a layered structure, with linear or nonlinear units, which can be trained by different optimization methods to minimize defined error function, and can be generated from, a large number of inputs. Neural networks are generally presented as systems of interconnected "neurons" which exchange messages between each other. The connections have numeric, weights that can be tuned based on feedback to the system, making neural networks adaptive to inputs and capable of learning from examples. Likewise, it will be understood that a decision tree is a predictive module that maps observations about an item or input to conclusions about the items' or inputs' target value. Decision tree learning is a modeling, approach often used in data mining and machine learning, and includes classification tree approaches where the target variable can take a finite set of branches in each layer, and the classification can be reached by going through limited number of layers of trees, and regression, which is one of the most general statistical approaches where the target variable can take continuous values. It will also be understood that the interpretation modules 24 and 28 may be trained using a complete supervised learning—including many of the algorithm-types mentioned above—or a combination of unsupervised and supervised learning—such as supervised, learning based on Principal Component Analysis generated feature sets, or a Deep Learning method which can have relatively more layers. The learning occurs based on existing datasets having, correctly-identified interpretations of waveforms used as correct observations, or examples, upon which a classifier is trained. The general interpretation module 24 and the cluster interpretation module 28 may be constructed and trained by any of the above-listed machine learning methods, and may be trained and constructed by the same method or by differing methods.

Figure 4:
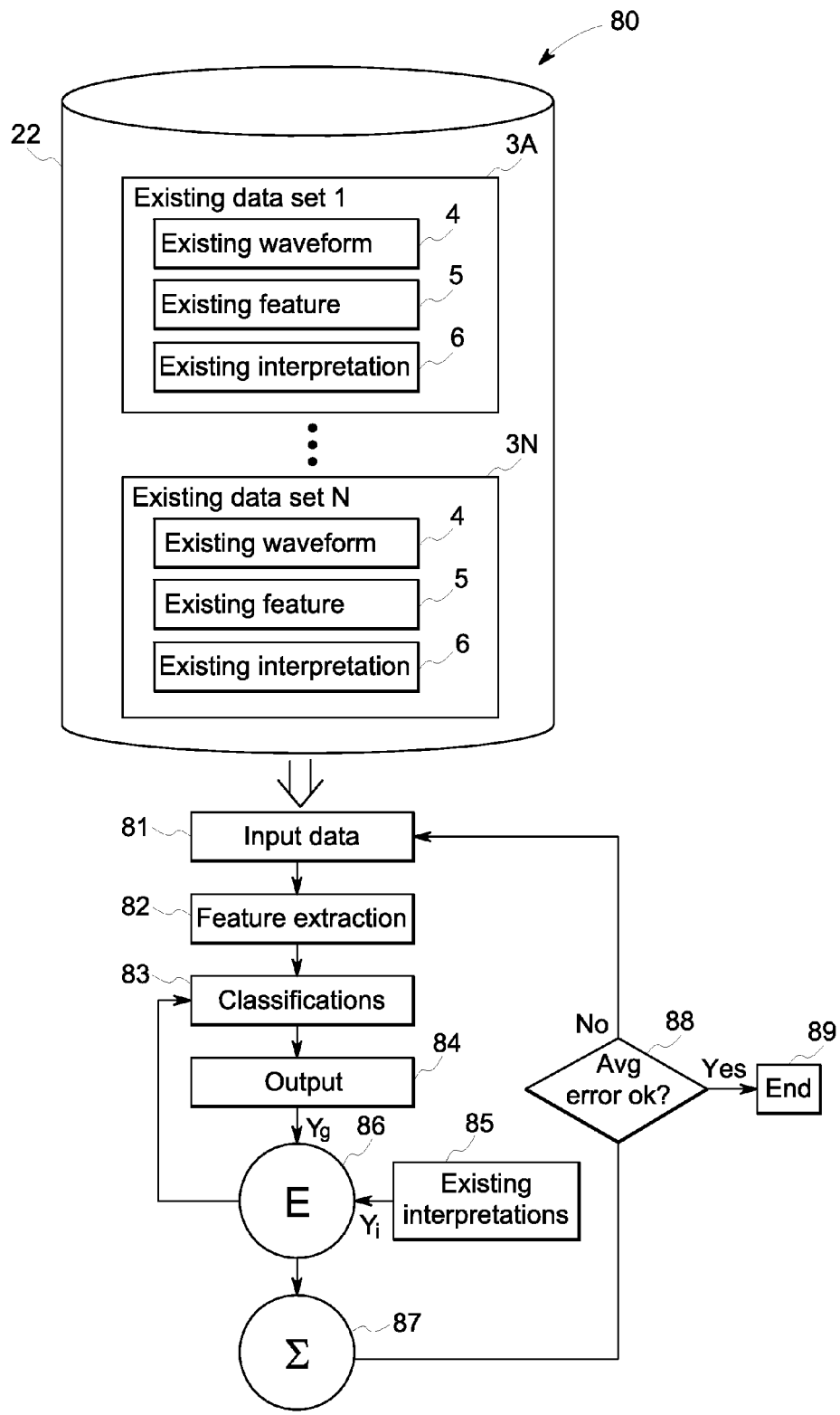
FIG. 4 depicts an exemplary method of training a general input module.

The general interpretation module 24 and the cluster interpretation module 28 differ from one another in that they are trained using different sets of data. The general interpretation module 24 is trained on a general database of existing ECG datasets, including datasets having any and all different types of waveform morphologies indicating any and all different diagnosis classifications. Referring also to FIG. 4, a general database 22 includes existing datasets 3a-3n. Each existing dataset 3 includes an existing ECG waveform 4. The existing ECG waveform may be the raw digitized ECG data, or it may include an ECG waveform that has been processed or conditioned for analysis, such as filtered to remove noise. Associated with each existing ECG waveform 4 is at least one existing feature 5 and existing interpretation 6 corresponding therewith. Each existing feature 5 is extracted from the existing ECG waveform 4 using feature extraction techniques. One of ordinary skill in the art will understand in light of this disclosure that multiple feature extraction techniques are available in the art and may be appropriate for applications in the presently disclosed system and method. For example, the feature extraction may determine the amplitudes and intervals in one or more portions of the ECG waveform, including each of the PQRST segments. Global features may include, but are not limited to, heart rate, QRS duration, PR interval, OT/QTc interval, etc. Lead-by-lead features may include, but are not limited to, P/QRS/ST/T/U wave durations, amplitude, and timing information. Rhythm features may include, but are not limited to synchronized and unsynchronized P wave (sinus, atrial arrhythmia, AFIB/Aflutter), QRS beat patterns (normal, bundle branch block, PVC, VT/VF), and T wave and its variations. Each existing dataset 3a-3n also includes at least one existing interpretation 6 of the existing ECG waveform 4, which preferably has been inputted by or verified by a clinician to insure accuracy. The existing interpretation 6 provides a classification, or diagnosis, of a physiological condition based on the one or more existing features 5 of the existing ECG waveform 4. Thus, the general database 22 includes existing datasets 3a-3n with all sorts of existing features 5 and existing interpretations 6 and is not defined or separated according to particular features 5.

The cluster database 20, on the other hand, which is used by a cluster training module 26 to train one or more cluster interpretation modules 28, includes datasets 3a-3n that are organized into clusters 10, which are a groups of existing ECG datasets 3a-3n having a common existing feature 5. A cluster database 20 is exemplified in FIG. 3, wherein clusters 10, 10' are groups of existing datasets 3a-3n with a common existing feature 5a-5n. As demonstrated in the figure, cluster 10 includes existing dataset 3a and existing, dataset 3b, which both share an existing feature 5a' and 5b' of "pathologic Q wave." Likewise, the cluster 10' includes the existing datasets 3a, 3b, and 3n, which all share the existing feature 5a, 5b, and 5n of "ST elevation." As is discussed in more detail below, a cluster interpretation module 28 is trained on one cluster 10, and thus is trained on a group of existing datasets 3a-3n that share a common existing feature 5. Accordingly, an appropriate cluster interpretation module 28 is chosen for application to the new ECG waveform 17 based on one or more features in that new ECG waveform, which is also explained in more detail below.

The new ECG waveform 17 and the one or more features 14 are processed by the general interpretation module 24 in order to produce a general interpretation output 34, which is an output describing a cardiac pathology or diagnosis which the general interpretation module 24 has arrived at based on the feature(s) 14 of the new ECG waveform 17. Likewise, the new ECG waveform 17 and feature(s) 14 are processed in the cluster interpretation module 28 in order to produce a cluster interpretation output 32, which is the physiologic classification or diagnosis generated by the cluster interpretation module 56 based on one or more of the features 14 isolated from the new ECG waveform 17. In one preferred embodiment illustrated in FIG. 2, the cluster interpretation module 28 is selected based on a single feature 14, or a group of features 14 appearing together and whose joint appearance has pathological significance.

The general interpretation output 34 and the cluster interpretation output 32 can then be compared to one another. The general interpretation output 34 and the cluster interpretation output 32 may be the same, or they may be different. Both of the outputs 32 and 34 may be presented to a clinician for analysis one at a time. For example, assuming that the general interpretation output 34 is different than the cluster interpretation output 32, the clinician may choose the output that is more accurate. For example, the clinician may be presented with an option to choose the cluster interpretation output 32. If they agree with the cluster interpretation, then this new ECG and its feature set will be added to the cluster to enhance the confidence level for this feature set with the related interpretation. If the clinician disagrees with the cluster interpretation, then the general interpretation output 24 will be presented. This option may be presented, for example, on a user interface 1210, and the clinician may provide input 12a, 12b regarding one or more of the cluster interpretation output 32 and the general interpretation output 24. If the clinician provides input 12a choosing the cluster interpretation output 32, the cluster interpretation module 28 may be updated to account for the information learned from interpreting the new ECG waveform 17 and associated feature(s) 14 by providing positive feedback based on the verification that the cluster interpretation output 32 was correct. Likewise, if the clinician provides input 12b to choose the general interpretation output, then the general interpretation module 63 may be updated, providing positive feedback that the general interpretation output 64 provided based on the new ECG waveform 17 was correct. In one embodiment, the clinician may be provided with the options to choose the respective outputs in sequence, where the general interpretation output 34 is only presented if the cluster interpretation output 32 is rejected. The options could be presented in either order, and thus an alternative arrangement may present the general interpretation output 34 first. In further embodiments, if the clinician provides input 12a, 12b selecting "no" to either option, rejecting the respective output 32 or 34, negative feedback may be provided to that respective module 28 or 24 based on the fact that the output 32, 34 was rejected as incorrect. Accordingly, in one embodiment, if the clinician provides "no" input 12a to reject the cluster interpretation output 32, negative feedback is provided to the cluster interpretation module 28; and if the clinician provides "no" input 12b to reject the general interpretation output 34, then negative feedback is provided to the general interpretation module 24. However, in other embodiments, and in accordance with the depiction in FIG. 1, only positive feedback may be provided.

Alternatively or in addition to providing feedback, if the clinician provides "no" input 12a and 12b rejecting both outputs 32 and 34, then a new cluster 38 may be created in the cluster database 20. In such an embodiment, a new dataset would be added to the cluster database 20 containing the new ECG waveform 17 and a cluster designated by the feature 14 upon which the cluster interpretation module 28 producing the rejected cluster interpretation output 32 was selected. Additionally, a noise outlier check may be performed to verify that the newly added cluster is not an 'outlier' caused by excessive noise from muscle, power line interference, saturation, drifted baseline, etc.

FIG. 2 demonstrates an embodiment of a method 50 of adaptive interpretation of ECG waveforms. In the depicted embodiment, a new ECG waveform data 17 is received at step 51. The new ECG waveform 17 is then processed with a feature extraction algorithm, or module, at step 52. As described above, feature extraction is well known in the art, and multiple different feature extraction methods and systems are available. For example, feature extraction may determine the amplitudes and intervals for each segment of a PQRST waveform. One or multiple features 14 may be extracted at step 52 from any given new ECG waveform 17. The extracted feature(s) 14 and/or the new ECG waveform data 17 are then processed by the cluster training module 26 according to the steps of the depicted embodiment. At step 53, one of the features 14 extracted at step 52 is automatically selected by the cluster training module 26. For example, the cluster training module 26 may select the feature 14 that is most prominent in the new ECG waveform data 17, such as the feature with the greatest relative deviation from a normal range. Alternatively or additionally, the cluster training module 26 may have a predetermined hierarchy of features 14, and thus may be programmed to select certain features over others. Alternatively or additionally, the cluster training module 26 may have only have access to cluster interpretation modules 28 for a limited number of features 14, and may be configured to select, those features 14 for which it has trained interpretation algorithms.

Once a feature 14 has been selected, the cluster training module 26 searches for a cluster interpretation module 28 associated with that feature 14 at step 54. For example, the cluster training module 26 may search for a cluster interpretation module 26 based on a cluster 10 (FIG. 3) of existing datasets 3a-3n having a shared existing feature 5 that matches identically to the feature 14 selected at step 53. Alternatively, the cluster training module 26 may be configured such that if an exact match is not located, a cluster interpretation module 28 based on a cluster 10 designating a similar existing feature 5 may be chosen at step 54. The degree of similarity required may vary, and may depend, for example, on the number of cluster interpretation modules 28 available to the cluster training module 26 and/or die level of development of the cluster database 20. If a cluster interpretation module 28 is found at step 54, the cluster training module 26 selects that cluster interpretation module 28 at step 55, and then processes the new ECG waveform 17 and/or the selected feature 14 with the selected cluster interpretation module 28 at step 56. At step 57, a cluster interpretation output 32 is provided, and then the cluster interpretation output 32 is displayed at step 58. The clinician then provides input 12a regarding the displayed cluster interpretation output 32, which is received at step 59. The clinician input 12a is analyzed at step 60 to determine whether the clinician input accepts or rejects the cluster interpretation output 32.

If the cluster interpretation output 32 is accepted at step 60, then the cluster training module 26 directs that the selected cluster interpretation module 28 be updated at step 61, such as to provide positive feedback reinforcing the process by which the cluster interpretation module 28 arrived at the cluster interpretation output 32, which was confirmed by the clinician to be correct. Then, at step 62, a new dataset is added to the cluster database 20 and is associated with the cluster 10 related to the cluster interpretation module 28 selected at step 54. The new dataset comprises the new ECG waveform received at step 51 and the feature selected at step 53, as well as the cluster interpretation output provided at step 57 and verified at step 60. Additionally, other features extracted at step 52 may also be included as part of the dataset.

If at step 60 it is determined that the clinician input 12a received at step 59 rejects the cluster interpretation output 32, then, in the depicted embodiment of FIG. 2, the method 50 continues to step 63, where the new ECG waveform 17 and extracted features 14 are processed with the general interpretation module 24. The general interpretation module will receive the new ECG waveform 17 and/or the one or more features 14 extracted at step 52, which is represented by the dashed line 36. In alternate embodiments, the general interpretation module may be used at step 63 to process only the feature selected at step 53 in the cluster training module 26, or the general interpretation module may be employed at step 63 to process all of the features extracted at step 52. In an embodiment where multiple features are extracted at step 52, and thus multiple features could be selected at step 53, the steps 53-62, or 53-71, may be repeated for each feature extracted at step 52.

Figure 5:
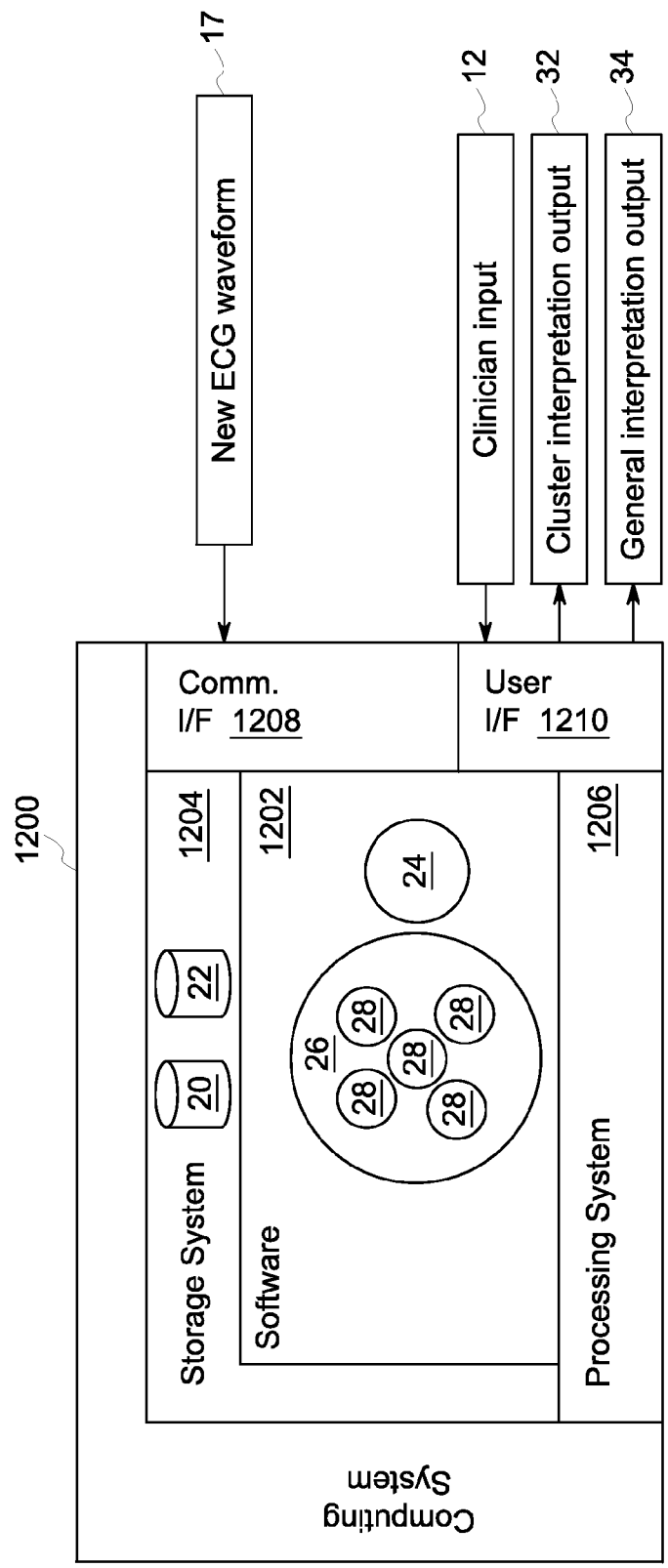
FIG. 5 diagrammatically depicts an exemplary system for adaptive interpretation of ECG waveforms.

At step 64, a general interpretation output 34 is provided by the general interpretation module 24. The general interpretation output 34 is then displayed at step 65, such as a display on user interface 1210. At step 66, a clinician input 12 is received, such as via the user interface 1210 (FIG. 5). At step 67, it is determined whether the clinician input 12 selects or confirms the general interpretation output 34. If the general interpretation output 34 is accepted, then the general interpretation module 24 is updated to provide positive feedback regarding the process executed by the general interpretation module 24 that led to providing, the general interpretation output 34 based on the new ECG waveform 17 and the extracted features 5.

On the other hand, if at step 67 the clinician input 12b rejects the general interpretation output 34, then the method continues to step 69, where a new interpretation is received from the clinician. The new interpretation from the clinician includes one or more interpretations of the new ECG waveform 17, such as diagnoses and/or pathologies indicated by the morphology and/or sinus rhythm recorded in the various leads of the new ECG waveform 17. Then, at step 70, a new cluster 38 is created in the cluster database relating to the feature or features 5 extracted at step 52. At this point, a noise outlier check may also be performed to verify that the newly added cluster is not a 'outlier' caused by excessive noise from muscle, power line interference, saturation, drifted baseline, etc. Finally, at step 71, a new ECG dataset is stored in the cluster database 20, for example, if noise outlier is ruled out. The new ECG dataset is in the new cluster 38 and includes the new ECG waveform 17 received, at step 51, the features 5 extracted at step 52, and the new interpretation from the clinician received at step 69.

Figure 3:
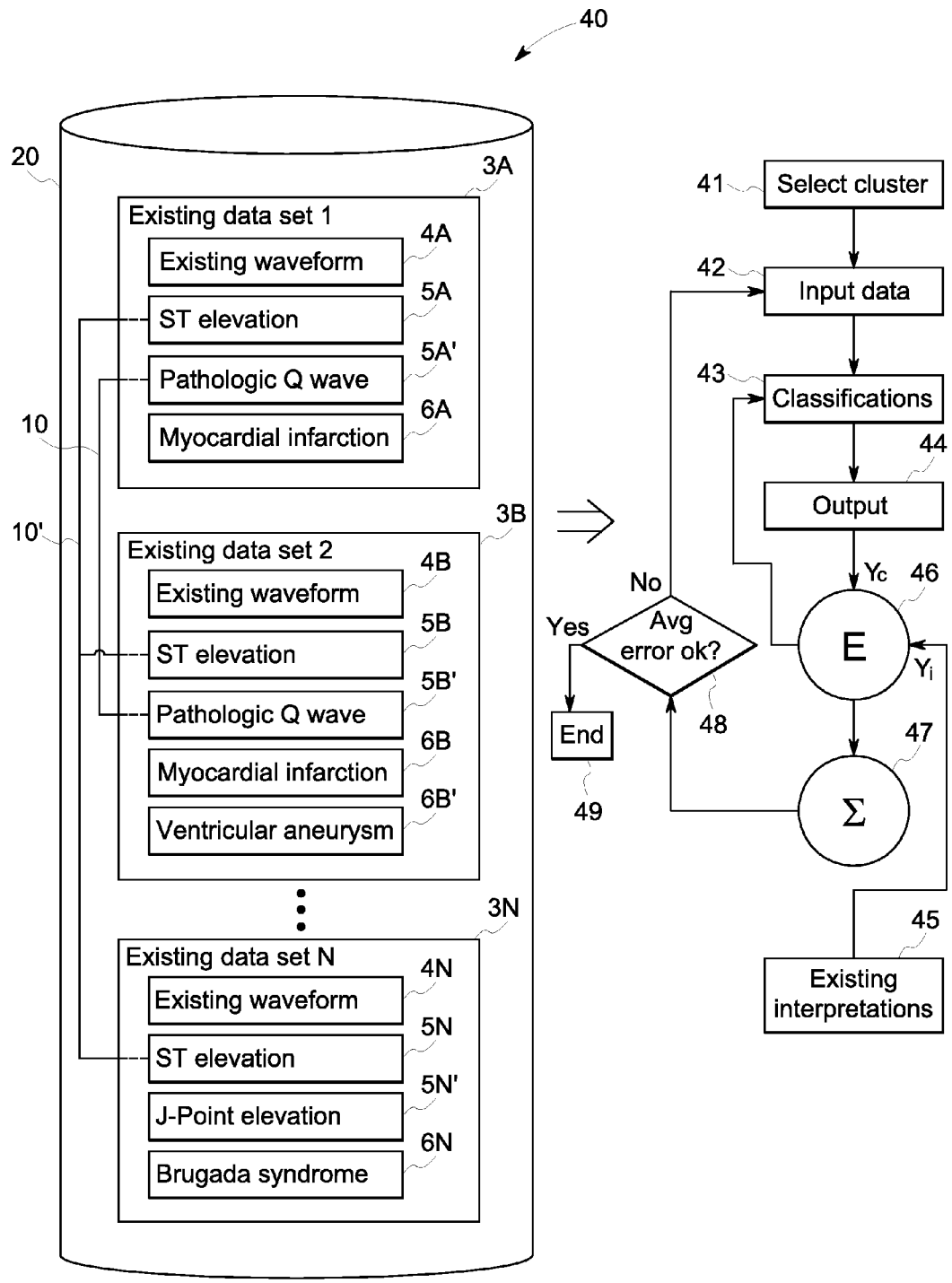
FIG. 3 depicts an exemplary method of training cluster modules.

FIG. 3 depicts a method 40 of training one or more cluster interpretation modules. At step 41, a cluster 10 is selected from the cluster database 20. At step 42, an existing dataset 3a-3n is selected and inputted into the cluster interpretation module 28. The cluster interpretation module 28 then determines classifications, such as diagnoses or patient physiologies associated with the existing datasets 3a-3n, executed at step 43. Depending on the embodiment of the training algorithm, the classification may be given various weights, such as confidence values. The classifications are then analyzed at step 44 to create an output. For example, at step 44, the classifications may be analyzed and classifications with low values, such as low confidence values, may be eliminated. As an illustrative example, at step 44, the classifications produced at step 43 may be filtered so that only classifications having values exceeding 50% confidence value become outputs. For a high specificity interpretation, a threshold of 80% confidence can be used. At step 45, the existing interpretations 5 associated with the respective datasets 3a-3n are received, and at step 46 the existing interpretations $Y_i$ are compared with the outputs $Y_e$ from step 44. For example, if the one or more outputs $Y_e$ from step 44 match any existing interpretation $Y_i$, then the output is valid and a value of 1 may be generated. For each output. $Y_e$, if the respective output $Y_e$ does not match any existing interpretation $Y_i$, then a value of 0 is generated. Accordingly, an error value E is generated at step 46. For example, where there are multiple outputs $Y_e$, the error value, represented with an ensemble of group of interpretation error between labeled values and calculated values from the system, with symbol E as an expectation value. Accordingly, the error expectation value E at step 46 may represent a fraction or a percent of the outputs $Y_e$ that are correct for that particular dataset 3. The error E generated at 46 for each output $Y_e$ is then provided as feedback to the cluster interpretation module 28 to adaptively change the coefficients of the learning system, and thus will affect future execution of step 43 for determining classifications. In an ideal case, the error expectation E is gradually reduced with the more data sets added, also called 'convergent'. The system may set an error boundary requiring that any future training shall not exceed a specified expectation error E. This process will guarantee that any evolving interpretation algorithm will not perform worse than a pre-trained one.

At step 47, an average error is generated for the system, which is an average of the error E for each output $Y_c$ generated by the cluster interpretation module 28 for this particular cluster 10. At step 48, it is determined whether the average error is within acceptable limits. If so, the training method 40 may come to an end at step 49. If the average error is too high, more input data associated with the cluster selected at step 41 is inputted at step 42 to further train the module.

As described above, each cluster 10 is a grouping of datasets 3 based on an existing feature 5. In the example provided in FIG. 3, two clusters 10, 10' are exemplified. Cluster 10 includes existing datasets 3a and 3b, which each share an existing feature 5a', 5b' of "pathologic Q wave". One of skill in the art will understand that various definitions of "pathologic Q wave" are available and known in the art, and may be applied within the methods and systems disclosed herein. Likewise, cluster 10' includes existing datasets 3a, 3b, 3n, as they all share existing feature 5a, 5b, 5n of "ST elevation." One of ordinary skill in the art will understand that various specific definitions of ST elevation are available in the art and any of the various definitions may be applied for use in the presently disclosed system and method. Moreover, each cluster 10, 10' may be based on more specific definitions or groupings of existing features 5, such as based on a more narrowly defined, or specific, waveform feature. In the context of the examples provided at FIG. 3, for example, each cluster 10, 10' may be defined based on a particular magnitude or morphology of ST elevation or pathologic Q wave. For example, the cluster 10, 10' may be based on a particular pattern of values seen in the Q wave segment or ST wave segment of each of the existing waveforms 4 of the existing datasets 3 in the cluster 10, 10'.

Alternatively or additionally, the cluster may be based on which leads the ST elevation or pathologic Q waves are located in. In an alternative embodiment, the method 40 of training a cluster interpretation module 28 may continue until all existing datasets 3a-3n in that cluster 10 are processed at least a prerequisite number of times, which may be one or more processing cycles of the entire cluster 10, 10'. As described above, the cluster interpretation module 28 may be any module trained by machine learning, such as a neural net or a decision tree. Accordingly, one of ordinary skill in the relevant art will understand that variations of the method 80 presented in FIG. 3 for training the cluster interpretation module 28 may be appropriate.

FIG. 4 depicts an embodiment of a method 80 of training a general interpretation module 24. At step 82, an existing dataset 3a, 3n is received. At step 81, the existing dataset 3a, 3n is processed with the general interpretation module 24 to generate classifications. At step 82, a feature extraction algorithm is run on the existing waveform 4 of the respective existing datasets 3a, 3n to extract features therefrom, in alternative embodiments, the training method 80 may instead utilize the existing features 5 for the training. At step 83, the feature extracted at step 82, or the existing features 5, and/or the existing waveform 4 of the respective existing dataset 3a, 3n are processed with the general interpretation module 24 to determine classifications. As described above, classifications may be, for example, diagnoses associated with the extracted features or the existing waveform. The classifications may be assigned values, such as weight or confidence values. Then, at step 84, one or more outputs $Y_g$ are determined based on the classifications, such as those classifications having an associated value exceeding a particular number. An error value E is then determined for the outputs by comparing, them to the existing interpretations received at step 85. The error value E determined at step 86 may be, for example, equal to 1 if the output $Y_g$ equals the existing interpretation $Y_i$, or equal to 0 if the output $Y_g$ does not equal at least one existing interpretation $Y_i$. Moreover, as explained above, multiple outputs $Y_g$ may be provided and may be compared to multiple existing interpretations $Y_i$. In such an example, the error F generated at step 86 may be an average of the error values generated for each output $Y_g$. The error value E may then be provided as feedback to reform the general interpretation module 24 and its next execution of the classifications step 83.

At step 87, the error values E generated for all input data may be summed and tracked. At step 88, it may be determined whether the average error value has reached an acceptably low limit. If it has, the training may be terminated at step 89. If the average error value remains high, then the training method 80 may continue until the error value is within acceptable limits. In an alternative embodiment, the method 80 of training the general interpretation module 24 may continue until the entire database 22, including the existing datasets therein 3a-3n are processed a predefined number of times, which may be one or more processing cycles. As described above, the general interpretation module 24 may be any module trained by machine learning, such as a neural net or a decision tree. Accordingly, one of ordinary skill in the relevant art will understand that variations of the method 80 presented in FIG. 4 for training the general interpretation module 24 may be appropriate. In an ideal case, the error expectation E is be gradually reduced with the more data sets added, also called 'convergent'. As described above, the system may set an error boundary for future training which will guarantee that any evolving interpretation algorithm will not perform worse than a pre-trained one. Thus, if the evolving system cannot reach convergence, the system can always resume to its pre-trained status, FIG. 5 is a system diagram of an exemplary embodiment of the system 1 for adaptively interpreting ECG waveforms including a cluster training module 26, a cluster interpretation module 28, and a general interpretation module 24 executable as described herein. The system 1 includes a computing system 1200 that includes a processing system 1206, storage system 1204, software 1202, communication interface 1208 and a user interface 1210. The processing system 1206 loads and executes software 1202 from the storage system 1204, including the cluster training module 26, cluster interpretation module 28, and general interpretation module 24, which are applications within the software 1202. Each of the cluster training module 26, cluster interpretation module 28, and general interpretation module 24 include computer-readable instructions that, when executed by the computing system (including the processing system 1206), direct the processing system 1206 to operate as described in herein in further detail, including to provide a cluster interpretation output 32 and a general interpretation output 34.

Although the computing system 1200 as depicted in FIG. 5 includes one software 1202 encapsulating one cluster training module 26, cluster interpretation module 28, and general interpretation module 24, it should be understood that one or more software elements may encapsulate the respective modules, and that each module 24, 26, 28 may be comprised of several software modules to execute the methods and operations described herein for each module. Similarly, while description as provided herein refers to a computing system 1 and a processing system 1206, it is to be recognized that implementations of such systems can be performed using one or more processors, which may be communicatively connected, and such implementations are considered to be within the scope of the description. For example, the cluster training module 26, cluster interpretation module 32, and/or general interpretation module 24 may be embedded into a device, like a cardiograph with local or remote database connection, or may be housed in a data server with an analytics service, like an ECG management system. Alternatively, cluster training module 26, cluster interpretation module 32, and/or general interpretation module 24 may be built into a remote server system, like cloud service with large set of servers and analytics for speed, reliability, and scalability.

The processing system 1206 comprises one or more processors, which may be microprocessors and other circuitry that retrieves and executes software 1202 from storage system 1204. Processing system 1206 can be implemented within a single processor, or processing device, but can also be distributed across multiple processors or sub-systems that cooperate in existing program instructions. Examples of processing system 1206 include one or more general purpose central processing units, application-specific processors, and logic devices, as well as any other type of processor, combinations of processing devices, or variations thereof.

The storage system 1204, which includes the cluster database 20 and general database 22, can comprise any storage media, or group of storage media, readable by a processor of processing system 1206, and capable of storing software 1202. The storage system 1204 can include volatile and non-volatile, removable and non-removable media implemented in any method or technology for storage of information, such as computer-readable instructions, data structures, program modules, or other data. Storage system 1204 can be implemented as a single storage device but may also be implemented across multiple storage devices or sub-systems. For example, the software 1202 may be stored on a separate storage device than the databases 20, 22.

Further, the cluster database 20 and the general database 22 may be stored on the same storage devices, or separate storage devices. Moreover, to the extent that the cluster database 20 and the general database 22 have overlapping content, the content may be shared between databases—e.g. once instance of the content may be stored and referenced by both databases 20 and 22. Storage system 1204 can further include additional elements, such a controller capable, of communicating with the processing system 1206.

Examples of storage media include random access memory, read only memory, magnetic discs, optical discs, flash memory, virtual memory, and non-virtual memory, magnetic sets, magnetic tape, magnetic disc storage or other magnetic storage devices, or any other medium which can be used to storage the desired information and that may be accessed by an instruction execution system, as well as any combination or variation thereof, or any other type of storage medium. In some implementations, the store media can be a non-transitory storage media. In some implementations, at least a portion of the storage media may be transitory.

The user interface 1210 is configured to generate cluster interpretation output 32 and general interpretation output 34, and to receive clinician input 12. User interface 1210 includes one or more display devices, such as a video display or graphical display, that can display outputs 32, 34. User interface 1210 may further include any mechanism for receiving input from a clinician, such as a mouse, a keyboard, a voice input device, a touch input device, a motion input device for detecting non-touch gestures and other motions by a user, and other comparable input devices and associated processing elements capable of receiving user input from a clinician. Speakers, printers, haptic devices and other types of output devices may also be included in the user interface 1210.

As described in further detail herein, the system 1 receives one or more new ECG waveform data 17. The new ECG waveform data 17 may be recorded by patient monitor including electrodes, and the data may be in analog or digital form. In still further embodiments, the new ECG waveform data 17 may be an analog input received in real time or near-real time by the system 1.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:

1. A system for adaptive interpretation of ECG waveforms, the system comprising:
    a processor;
    a cluster database of existing ECG datasets organized into clusters, wherein each existing ECG dataset includes an existing ECG waveform with at least one corresponding existing feature and existing interpretation, and wherein the clusters are existing ECG datasets having a common existing feature;
    a user interface; and
    a cluster training module executable by the processor to:
        receive a new ECG waveform and a feature extracted from the new ECG waveform;
        select a cluster interpretation module based on the feature, wherein the cluster interpretation module is trained on one of the clusters from the cluster database;
        process the new ECG waveform and/or the feature to provide a cluster interpretation output;
        display the cluster interpretation output on the user interface;
        receive clinician input via the user interface accepting or rejecting the cluster interpretation output; and
        create a new cluster based on the extracted feature when the clinician input rejects the cluster interpretation output.

2. The system of claim 1, wherein the cluster training module is executable to further train the cluster interpretation module based on the clinician input.

3. The system of claim 1, further comprising a general interpretation module trained on a general database of existing ECG datasets, wherein the general interpretation module is executable by the processor to process the new ECG waveform and/or the extracted feature to provide a general interpretation output.

4. The system of claim 3, wherein the system is configured such that if the clinician input received by the cluster training module rejects the cluster interpretation output, then the general interpretation module displays the general interpretation output on the user interface.

5. The system of claim 4, wherein the general interpretation module is further executable by the processor to receive clinician input via the user interface accepting or rejecting the general interpretation output.

6. The system of claim 5, wherein the cluster training module is executable to create a new cluster based on the extracted feature if the clinician input rejects the cluster interpretation output and the general interpretation output.

7. The system of claim 3, wherein at least one of the general interpretation module and the cluster training module is a neural network or a decision tree.

8. A method for adaptive interpretation of ECG waveforms, the method comprising:
    receiving a new ECG waveform;
    extracting at least one feature from the new ECG waveform;
    selecting a cluster interpretation module based on the feature;
    processing the new ECG waveform and/or the extracted feature to provide a cluster interpretation output;
    displaying the cluster interpretation output on a user interface;
    receiving a clinician input via the user interface rejecting the cluster interpretation output; and
    using the clinician input as negative feedback to train the cluster interpretation module.

9. The method of claim 8, wherein the cluster interpretation module is trained on a cluster from a cluster database of existing ECG datasets, wherein each existing ECG dataset includes an existing ECG waveform with at least one corresponding existing feature and existing interpretation, and wherein each cluster is comprised of ECG datasets having a common existing feature.

10. The method of claim 9, further comprising creating a new cluster based on the extracted feature if the clinician input rejects the cluster interpretation output.

11. The method of claim 8, further comprising processing the new ECG waveform and/or the extracted feature with a general interpretation module to provide a general interpretation output, wherein the general interpretation module is trained on a general database of existing ECG datasets.

12. The method of claim 11, further comprising displaying the general interpretation output on the user interface.

13. The method of claim 12, further comprising receiving a clinician input accepting or rejecting the general interpretation output.

14. The method of claim 13, further comprising further training the general interpretation module based on the clinician input.

15. The method of claim 13, further comprising creating a new cluster based on the extracted feature if the clinician input rejects the cluster interpretation output and the general interpretation output.

16. The method of claim 8, further comprising an initial step of training at least one cluster interpretation module to provide the cluster interpretation output based on a cluster from a cluster database of existing ECG datasets, wherein each existing ECG dataset includes an existing ECG waveform with at least one corresponding existing feature and existing interpretation, and wherein each cluster is comprised of ECG datasets having a common existing feature.

17. A non-transitory computer readable medium having computer-executable instructions stored thereon, wherein the instructions include steps comprising:
   receiving a new ECG waveform;
   extracting at least one feature from the new ECG waveform;
   selecting a cluster interpretation module based on the feature;
   wherein the cluster interpretation module is trained on a cluster from a cluster database of existing ECG datasets, wherein each existing ECG dataset includes an existing ECG waveform with at least one corresponding existing feature and existing interpretation, and wherein each cluster is comprised of ECG datasets having a common existing feature;
   processing the new ECG waveform and/or the extracted feature with the cluster interpretation module to provide a cluster interpretation output;
   displaying the cluster interpretation output on a user interface;
   receiving a clinician input rejecting the cluster interpretation output; and
   further training the cluster interpretation module based on the clinician input rejecting the cluster interpretation output.

18. The non-transitory computer readable medium of claim 17, wherein the instructions include the steps further comprising:
   processing the new ECG waveform and/or the extracted feature with a general interpretation module to provide a general interpretation output, wherein the general interpretation module is trained on a general database of existing ECG datasets;
   displaying the general interpretation output on a user interface; and
   receiving a clinician input accepting or rejecting the general interpretation output.

19. The non-transitory computer readable medium of claim 18, wherein the instructions include the steps further comprising creating a new cluster based on the extracted feature if the clinician input rejects the cluster interpretation output and the general interpretation output.

* * * * *